US005662642A

United States Patent [19]

Isono et al.

[11] Patent Number: 5,662,642

[45] Date of Patent: Sep. 2, 1997

[54] INSTILLATOR WITH MEDICATOR-CONNECTING MOUTH

[75] Inventors: Keinosuke Isono, Saitama-ken; Tatsuo Suzuki, Tokyo, both of Japan

[73] Assignee: Material Engineering Technology Laboratory, Inc., Tokyo, Japan

[21] Appl. No.: 366,751

[22] Filed: Dec. 30, 1994

[30] Foreign Application Priority Data

Aug. 9, 1994 [JP] Japan .................................... 6-209204

[51] Int. Cl.[6] .................................................. A61B 19/00

[52] U.S. Cl. .......................... 604/403; 604/406; 604/408; 604/411

[58] Field of Search .................................... 604/403, 406, 604/408, 410–416

[56] References Cited

U.S. PATENT DOCUMENTS 5,108,702 4/1992 Hubner .................................... 604/415

FOREIGN PATENT DOCUMENTS 33 33 283 4/1985 Denmark .

0 116 362 8/1984 European Pat. Off. .

*Primary Examiner*—John G. Weiss

*Assistant Examiner*—Dennis Ruhl

*Attorney, Agent, or Firm*—Cushman Darby & Cushman IP Group of Pillsbury Madison & Sutro LLP

[57] ABSTRACT

An instillator having a medicator-connecting mouth into which a medication that cannot be subjected to sterilization may be introduced by a simple operation and in a germ-free condition so that the medication is mixed with a pharmaceutical liquid contained therein, said instillator being composed of an outlet member, a medicator-connecting mouth and a body, said medicator-connecting mouth comprising a communicating pathway which communicates with the inside of the body upon use, a germ-trapping filter disposed in the middle of said communicating pathway, a sealing means for sealing said communicating pathway disposed between said germ-trapping filter and said body, and a connecting means disposed at one end of said communicating pathway opposite to the body, the body made of a flexible material being filled with a pharmaceutical liquid, sealed and subjected to autoclaved sterilization, the connecting port of the instillator having a connecting duct tightly fitted into the port.

4 Claims, 11 Drawing Sheets

INSTILLATOR WITH MEDICATOR-CONNECTING MOUTH

BACKGROUND OF THE INVENTION (i) Field of the Invention

The present invention relates to an instillator for drip injection, which has a medicator-connecting mouth, i.e. a connecting mouth for mixing medications, and is used in the field of medication. In particular, it relates to an instillator for drip injection, into which a medication that cannot be subjected to sterilization may be introduced in a germ-free condition Just before its use, and the thus-introduced medication is mixed with the germ-free injection base contained in the instillator.

(ii) Description of Related Art

In general, medications in aqueous solutions that are extremely unstable and medications which decompose or deteriorate when subjected to thermal sterilization, for example, with high-pressure steam, etc. are stored as a powdery preparation. When such a medication is to be administered to a patient by drip injection, a dissolving liquid is first injected with an injector or the like into the container containing the medication powder to form a solution of the medication therein. The solution of the medication is then removed from the container, also with an injector or the like, and is introduced into an instillator and mixed with an injection base contained therein.

SUMMARY OF THE INVENTION

However, an operation consisting of such steps must be conducted in a germ-free condition which makes it extremely troublesome. The present invention has been devised so as to eliminate this difficulty, and its object is to provide an instillator having a medicator-connecting mouth, into which a medication that cannot be subjected to sterilization may be directly introduced in a germ-free condition to be mixed with an injection base contained therein.

The instillator with a medicator-connecting mouth of the present invention is composed of an outlet member, a medicator-connecting mouth to be connected to a medicator, and a body, said medicator-connecting mouth comprising a communicating pathway which communicates with the inside of the body upon use of the instillator, a germ-trapping filter disposed in the middle of said communicating pathway, a sealing means for sealing the communicating pathway at a portion of the communicating pathway nearer to the body than said germ-trapping filter, and a connecting means to said medicator formed at the end of the communicating pathway opposite (or distal) to the body.

The above-described sealing means of the instillator according to the present invention is provided inside said body and can be easily broken open so that the communicating pathway connects the inside of the body and the outside of the body.

Further, the medication in said medicator used in the instillator according to the present invention is typically a solid or liquid medication which deteriorates under sterilization.

Said connecting means of the instillator according to the present invention can be a needle or a needle guard rubber stopper.

The germ-trapping filter of the instillator according to the present invention preferably has a pore diameter of 0.2 μm or less.

The instillator according to the present invention is formed by filling a pharmaceutical liquid in the body thereof and subjecting the instillator body to autoclaved sterilization.

DETAILED DESCRIPTION OF THE INVENTION

Figure 1:
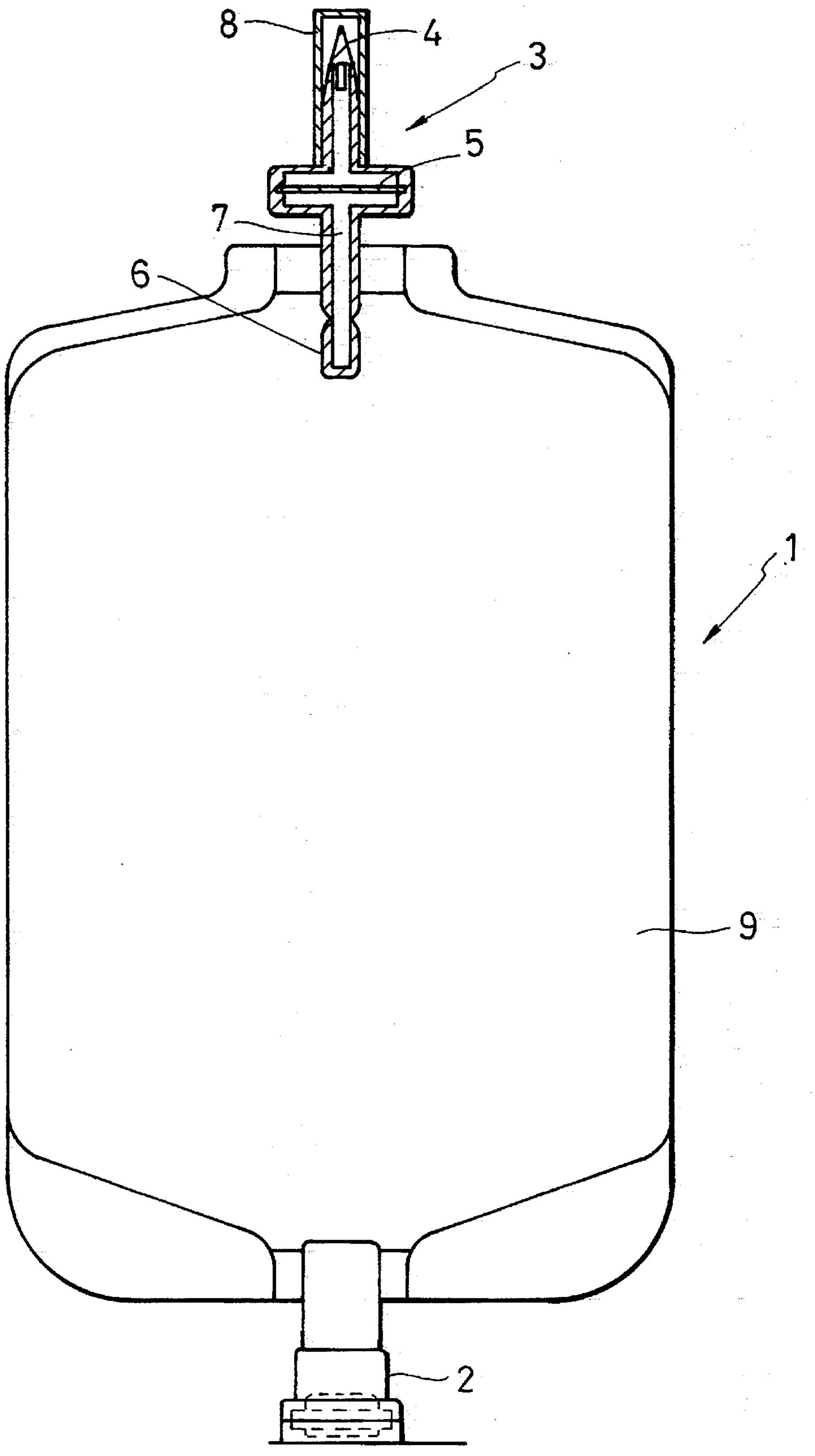
FIG. 1 is a sectional view showing an essential part of the first embodiment of the instillator of the present invention.

The instillator of the present invention is provided with a medicator-connecting mouth having a germ-trapping filter therein, and the body of the instillator and the medicator-connecting mouth are sterilized with high-pressure steam at the same time. The medicator-connecting mouth has a communicating pathway which extends inside the body of the instillator, a germ-trapping filter disposed in the middle of the communicating pathway, a sealing means disposed between the germ-trapping filter and the body for sealing the communicating pathway, and a connecting means disposed at one end of the communicating pathway opposite to the body. When the instillator is sterilized with high-pressure steam and while it is stored before use, the pharmaceutical liquid contained in the body of the instillator and the germ-trapping filter are kept separated from each other via the sealing means so that they are not brought into contact with each other.

Before the instillator of the present invention is used, the communicating pathway of the medicator-connecting mouth is closed by the sealing means inside the body. Therefore, the germ-trapping filter is not affected by a pharmaceutical liquid in the body while the instillator is stored. In consequence, the function of the germ-trapping filter is maintained normal just before the use of the instillator.

Further, where the sealing means is provided inside the body and also constitutes an easily steal-breaking means whereby the communicating pathway can be opened from the outside of the body, it is possible to seal the communicating pathway until the instillator is connected to a medicator. By opening the communicating pathway by a germ-free operation, the pharmaceutical liquid in the body is brought into contact with the germ-trapping filter for the first time.

Further, by using a germ-trapping filter having a pore diameter of 0.2 μm, it is possible to remove substantially germs and toxic fragments of pellicles and the like.

The above-mentioned connecting means may be either a communicating needle made of a synthetic resin or a rubber stopper. According to this, the instillator of the present invention may be combined with a medicator containing therein a powdery medication that cannot be subjected to sterilization and having, at its mouth, a rubber stopper or a communicating needle made of a synthetic resin. For instance, the instillator having, as the connecting means, a communicating needle made of a synthetic resin is combined with a medicator having, at its mouth, a rubber stopper. The medicator-connecting mouth of the instillator is attached to the mouth of the medicator, while the communicating needle of the former made of a synthetic resin is made to pierce through the rubber stopper at the mouth of the latter. Next, the sealing means is broken, by which the pharmaceutical liquid contained in the instillator is transferred into the medicator through the medicator-connecting mouth via the germ-trapping filter. Then, the medication is dissolved in the medicator, and thereafter the resulting medication solution is transferred into the instillator via the germ-trapping filter. In this process, even when the medicator contains germs, the content of the instillator is not contaminated by the germs since the medication solution is transferred into the instillator via the germ-trapping filter. In this way, it is possible to introduce a medication that cannot be subjected to sterilization into the instillator of the present invention without being contaminated by germs, and the thus-introduced medication may be mixed with the pharmaceutical liquid contained in the instillator in a germ-free condition.

EXAMPLES

Instillator 1 shown in FIG. 1, which is the first embodiment of the present invention, is composed of a body 9, an outlet member 2 and a medicator-connecting mouth 3. The medicator-connecting mouth 3 is composed of a connecting means 4, a germ-trapping filter 5, a sealing means 6 and a communicating pathway 7. The germ-trapping filter 5 is disposed in the middle of the communicating pathway 7. The connecting means 4 in this embodiment is a hollow, communicating needle made of a synthetic resin. The communicating needle made of a synthetic resin is covered with a cap 8.

The instillator 1 of the first embodiment of the present invention is a container which is to contain therein a dissolving liquid, a diluting liquid, a base liquid for drops, etc., and is made of a flexible material including, for example, low-density polyethylene resins, linear, low-density polyethylene resins, high-density polyethylene resins, polypropylene resins, soft polyester resins, chlorinated polyethylene resins, polyvinyl chloride resins, ethylene-vinyl acetate copolymers, etc. Of these, preferred are polyolefin resins such as low-density polyethylene resins, linear, low-density polyethylene resins, polypropylene resins, etc., since they have a high chemical resistance so that they release only few dissolved substances in the dissolving liquid to be contained in the instillator and since they are low-priced they are advantageous from the economical point of view.

The communicating needle as the connecting means 4 is made of polyolefinic resins, such as polyethylene resins or polypropylene resins, or styrenic resins, acrylic resins, polycarbonate resins, polyamide resins, etc. Since the sealing means 6 is kept in contact with the pharmaceutical liquid to be contained in the instillator 1, it is preferably made of polyethylene resins or polypropylene resins.

The germ-trapping filter 5 may be any commercial membrane filter through which germs do not pass. Any membrane filter having a pore diameter of 0.5 μm or less may trap germs. Particularly, membrane filters having a pore diameter of 0.2 μm or less can remove toxic fragments of broken germs. As the material of such a membrane filter, mentioned are cellulosic resins such as cellulose acetate, cellulose triacetate, regenerated cellulose, cellulose nitrate, cellulose-mixed esters, etc.; polycarbonate resins, polyamide resins, fluorine resins, polyvinylidene chloride resins; polyolefinic resins such as polyethylene resins, polypropylene resins, etc.

In this embodiment., the body of the instillator 1 is made of a tube formed by inflation molding. The outlet member 2 and the medicator-connecting mouth 3 are tightly hot-sealed to each end of the tube cut to have a predetermined size, through which no liquid passes. Into the instillator 1 hot-sealed with the medicator-connecting mouth 3 in this way, a pharmaceutical liquid is injected through the outlet member 2, and the member 2 is sealed with a rubber stopper. The instillator now containing the pharmaceutical liquid is sterilized in an autoclave. As examples of the dissolving liquid which the instillator 1 is to contain, mentioned are amino acid-containing liquids; high-calory base liquids for drops, consisting essentially of glucose, a physiological saline solution, 5% glucose solution, distilled water for injection, solutions containing various electrolytes, etc.

Figure 2:
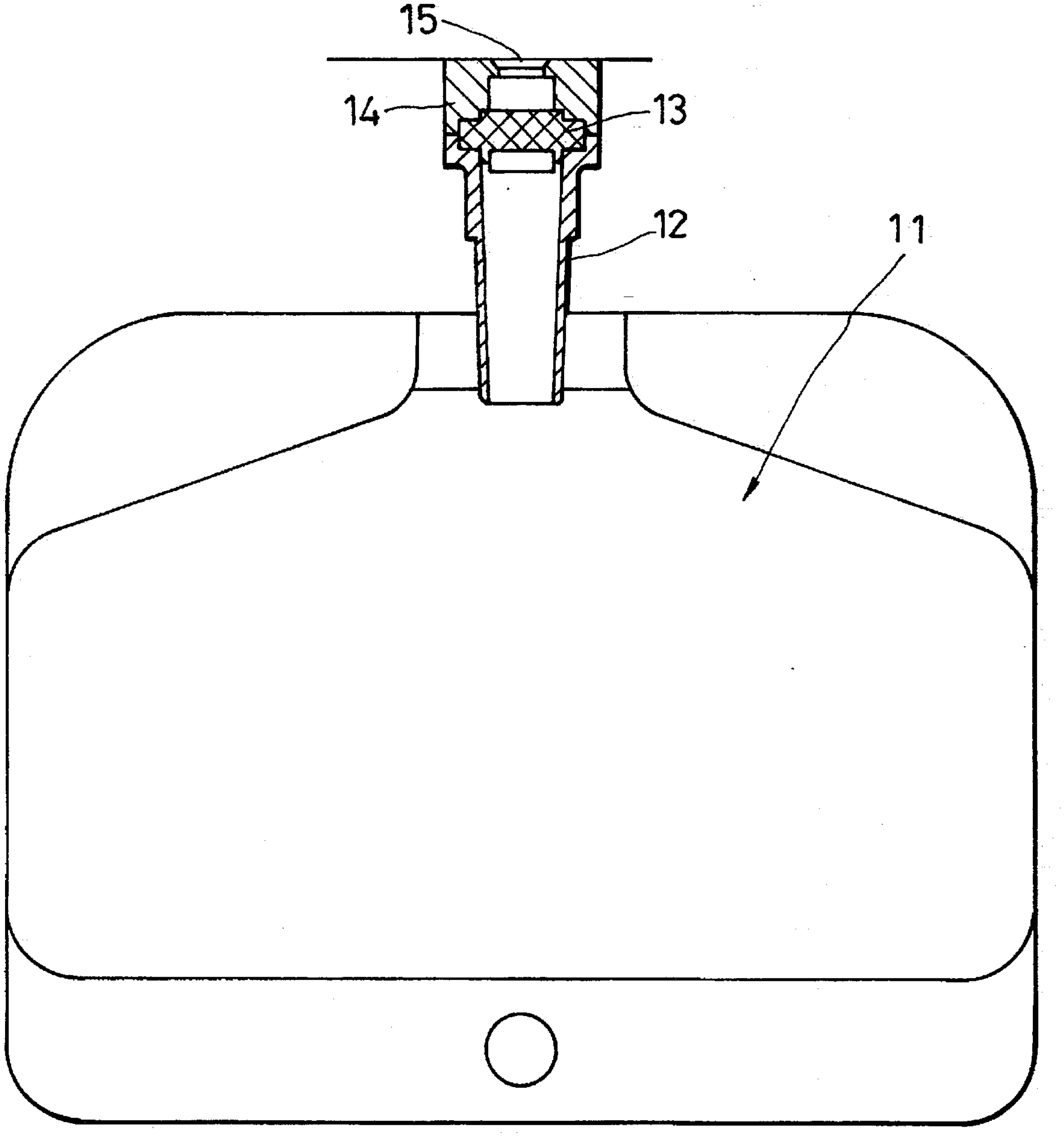
FIG. 2 is a sectional view showing an essential part of a medicator to be connected to the first embodiment of the instillator shown in FIG. 1.

FIG. 2 shows the first embodiment of a medicator applicable to the present invention, in which the medicator 11 is a container which is to contain a solid medication, such as a powdery medication, a freeze-dried medication, etc., or a liquid medication. The medicator 11 is a container made of a synthetic resin, and its mouth 12 is sealed with a stopper 13 and covered with a stopper cover 14. The medicator 11 illustrated by this embodiment is a flexible container which, however, is not intended to be limitative with respect to the present invention. The medicator 11 may be a vial made of a known material such as glass or synthetic resin. It is preferred that such a non-flexible medicator is provided with a part of a liquid-filtering membrane of a germ-trapping filter or, apart from a liquid-filtering membrane, a germ-trapping air filter (through which air passes even when it is kept in contact with liquid).

As one example of the medication to be in the medicator 11, mentioned is l-glutamine which is one of the amino acids. When ah aqueous solution of L-glutamine is heated to 100° C., it decomposes into pyrrolidone carboxylic acid. Therefore, it cannot be subjected to autoclaved sterilization. The present invention is applicable to such a medication that cannot be sterilized in the form of its aqueous solution.

Figure 3:
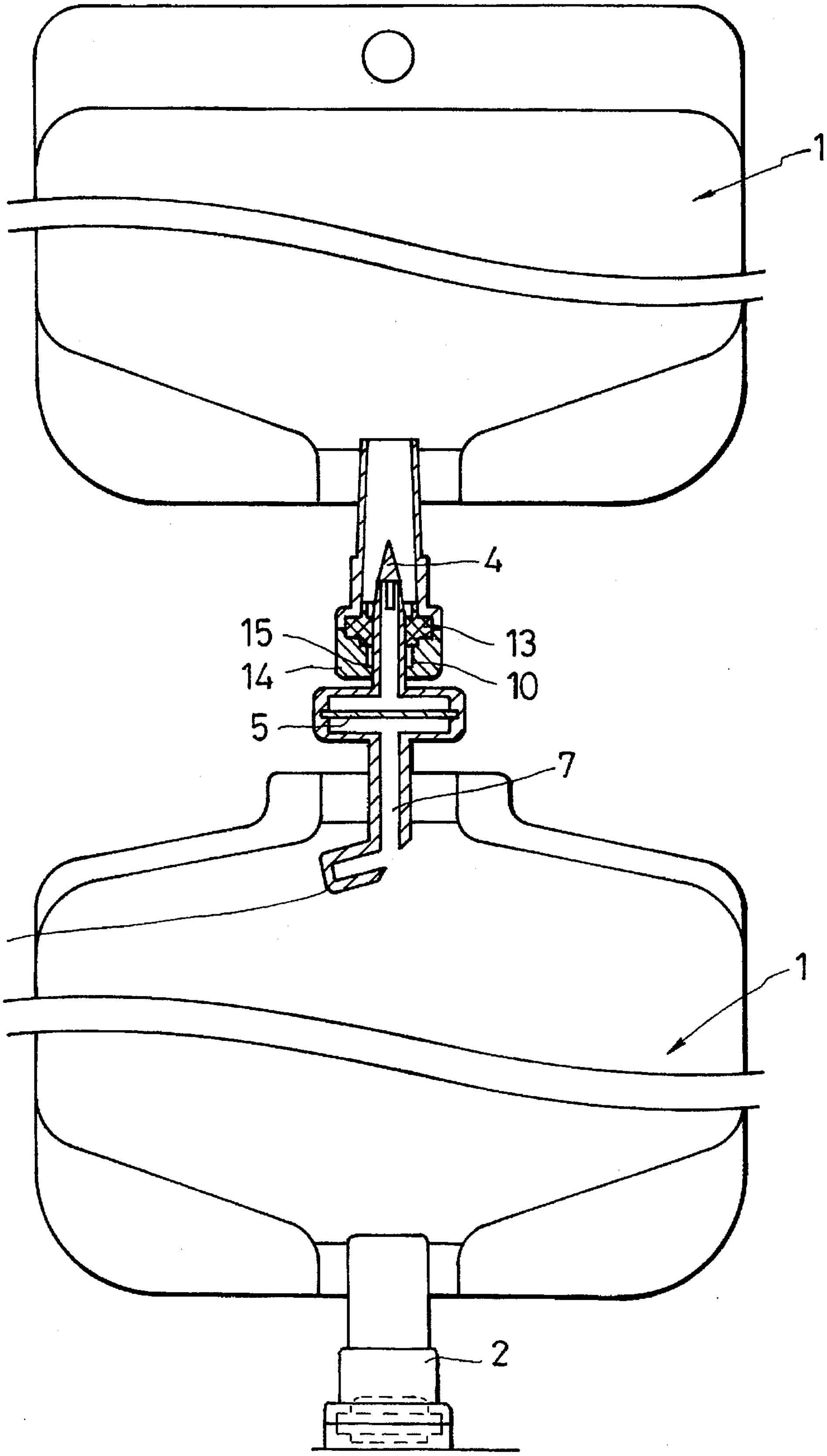
FIG. 3 is a sectional view showing an essential part of the connection between the first embodiment of the instillator and the medicator.

FIG. 3 shows the connection of the sealed instillator 1 containing therein a dissolving liquid sterilized by autoclave sterilization to the sealed medicator 11 containing therein a medication. The cap 8 is removed from the communicating needle. The communicating needle, namely the connecting means 4 is put into the stopper 13, and is inserted into the mouth of the medicator until the projection 10 of the connecting means runs over the projection 15 of the stopper cap. Next, the weakened portion of the sealing means 6 is broken by bending it from the outside of the instillator 1, and the inside of the instillator 1 communicates with the inside of the medicator 11 via the communicating pathway 7. Afterwards, the instillator 1 is pressed or rubbed so that a part of the dissolving liquid contained in the instillator 1 is transferred into the medicator 11 through the communicating pathway 7 via the germ-trapping filter 5, and the medication in the medicator 11 is dissolved in the thus-transferred dissolving liquid. Then, the medicator 11 is pressed or rubbed so that the thus-dissolved medication therein is transferred into the instillator 1 through the communicating pathway 7 via the germ-trapping filter 5. Even though the solution of the medication prepared in the medicator 11 contains germs, the inside of the instillator 1 is not contaminated by such germs since the solution is transferred into the instillator 1 via the germ-trapping filter 5. A dripping kit is fitted into the outlet member 2 of the instillator 1, through which the solution of the medication is administered to a patient by drip injection.

Figure 4:
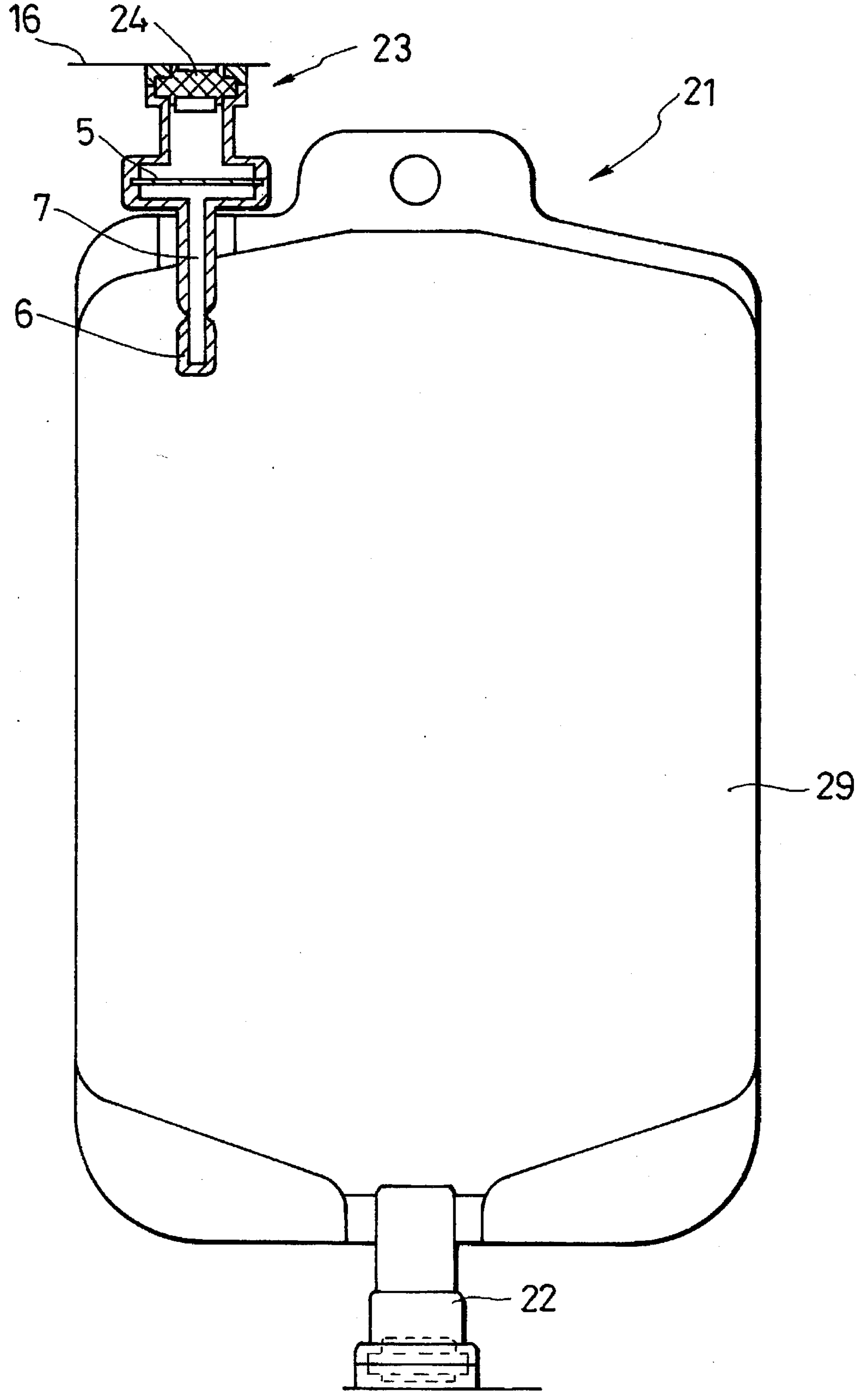
FIG. 4 is a sectional view showing an essential part of the second embodiment of the instillator.

Instillator 21 shown by FIG. 4 is the second embodiment of the present invention. The instillator 21 is composed of a body 29, a outlet member 22 and a medicator-connecting mouth 23. The medicator-connecting mouth 23 is composed of a connecting means 24, a germ-trapping filter 5, a sealing means 6 and a communicating pathway 7. The germ-trapping filter 5 is disposed in the middle of the communicating pathway 7. The connecting means 24 in this embodiment is composed of a rubber stopper and a stopper cap. The cap is covered with a protective sheet 16. Also in this embodiment, the body of the instillator 21 is made of a tube formed by inflation molding, like that in the first embodiment.

Figure 5:
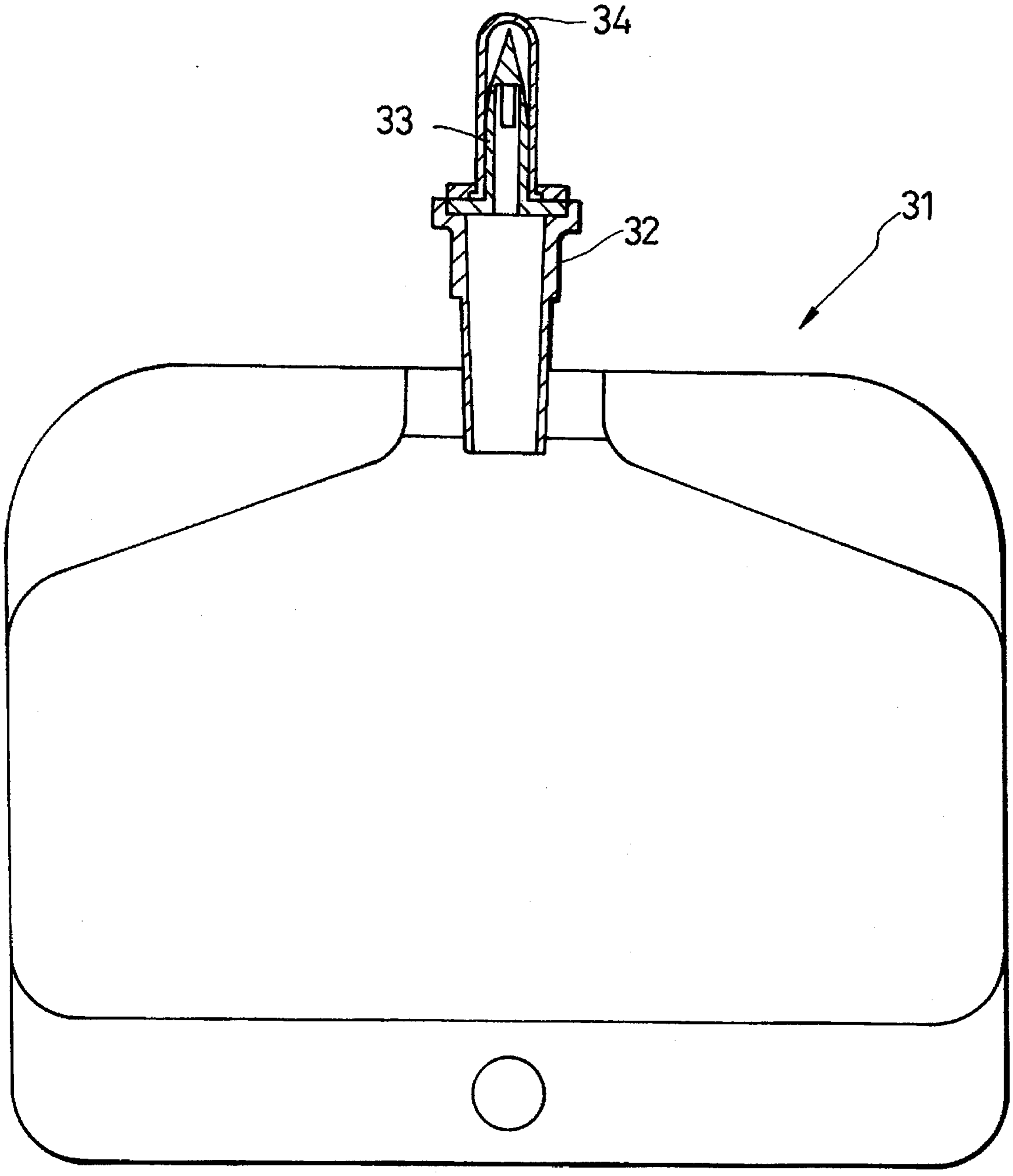
FIG. 5 is a sectional view showing an essential part of a medicator to be connected with the second embodiment of the instillator of FIG. 4.

FIG. 5 shows the second embodiment of medicator 31. The medicator 31 is a flexible container made of a synthetic resin, and its mouth 32 is fitted with a hollow, communicating needle 33 made of a synthetic resin. The mouth of the needle 33 is sealed with a rubber cap 34.

Figure 6:
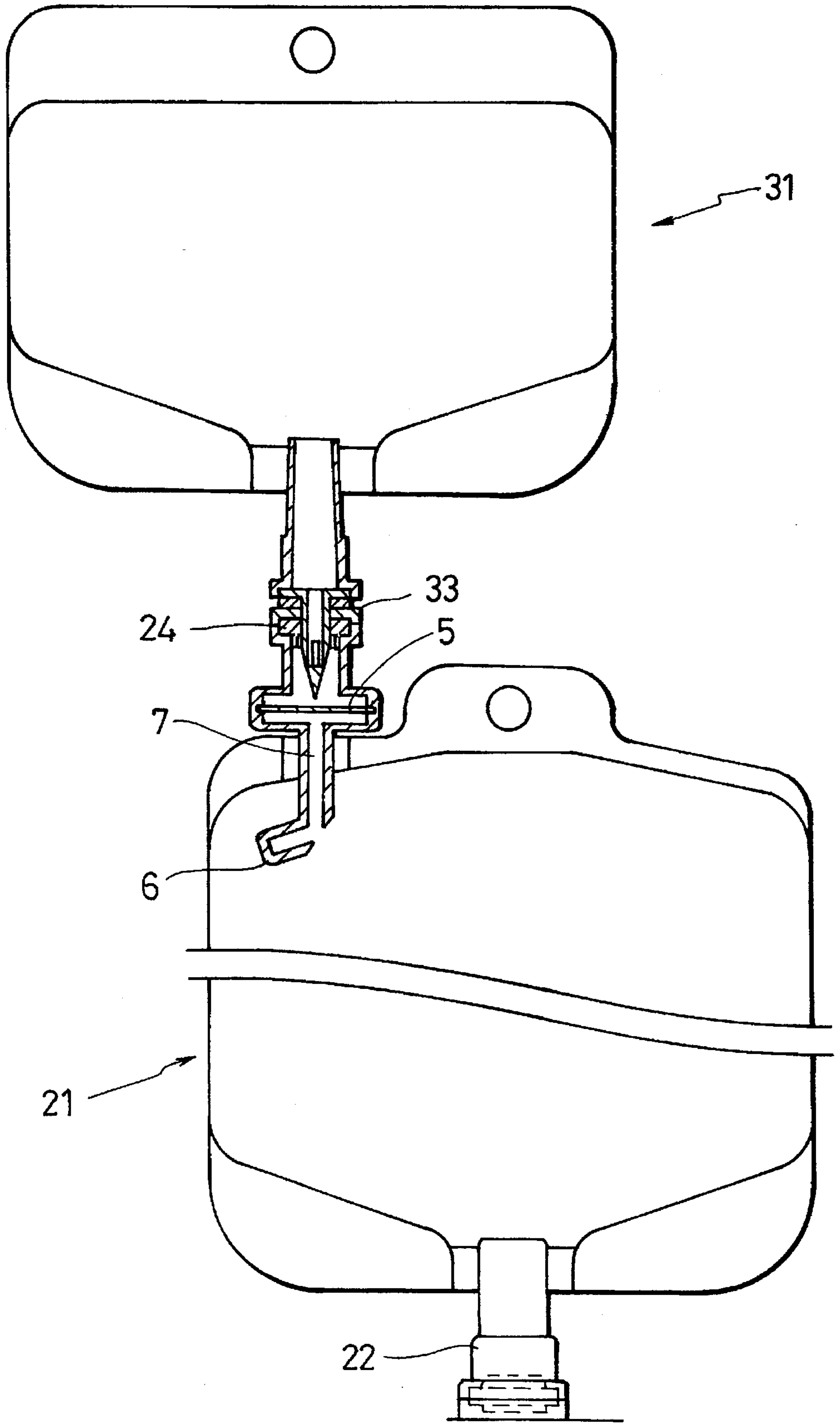
FIG. 6 is a sectional view showing an essential part of the connection between the second embodiment of the instillator and the medicator.
Figure 7:
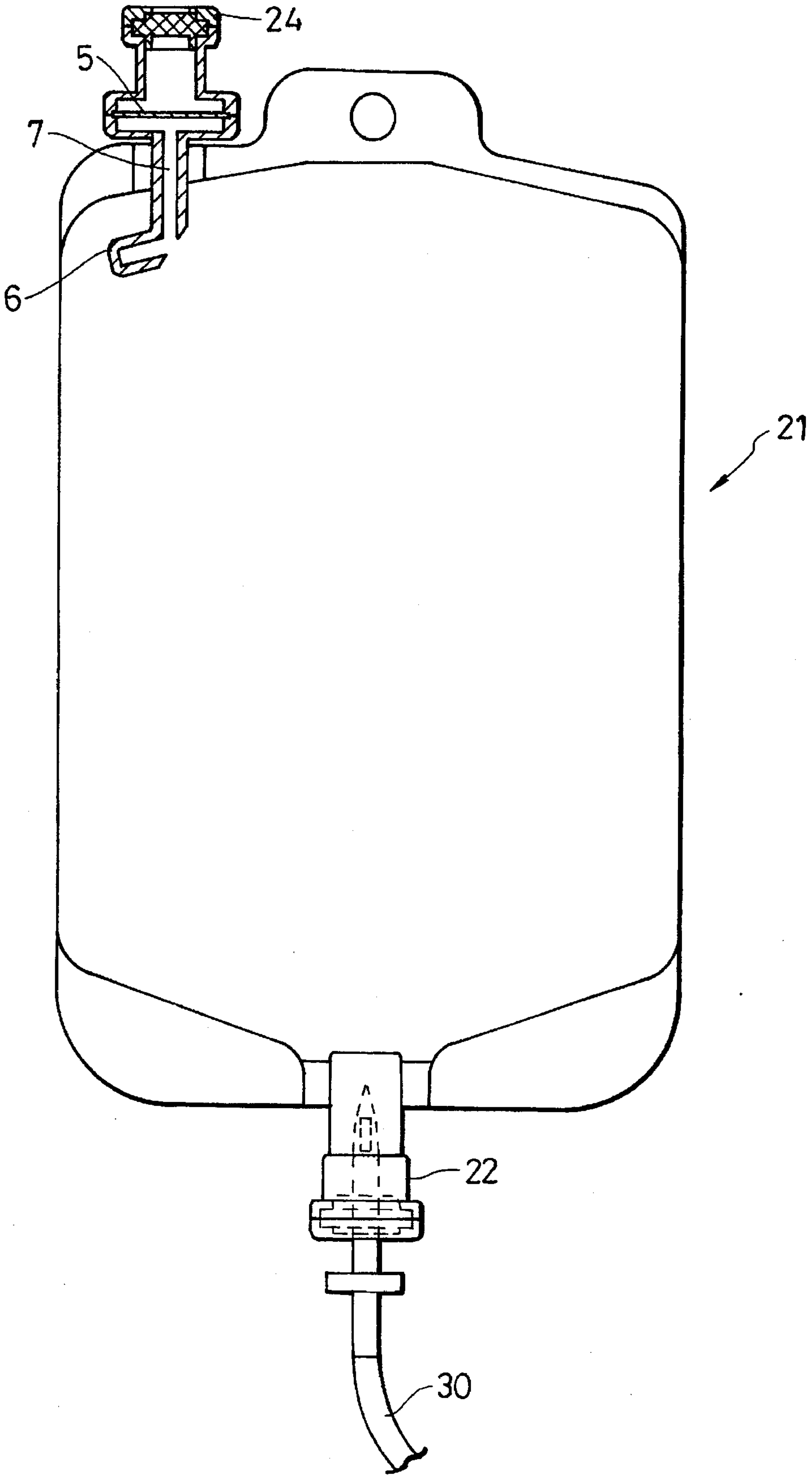
FIG. 7 is a sectional view showing an essential part with the medicator removed from the second embodiment of the instillator of FIG. 4, into which a medication had been introduced and mixed with the pharmaceutical liquid contained therein, (a dripping kit has also been connected to the instillator).

FIG. 6 shows the connection of the sealed instillator 21 containing therein a dissolving liquid sterilized by autoclave sterization to the sealed medicator 31 containing therein a medication. The protective sheet 16 is peeled, and the communicating needle 33 of the medicator is put into the rubber stopper, namely, the connecting means 24. The communicating needle 33 pierces the rubber cap 34 and then runs through the rubber stopper, namely the connecting means 24. Next, the weakened portion of the sealing means 6 is broken by bending it from the outside of the instillator 21, and the inside of the instillator 21 communicates with the inside of the medicator 31 via the communicating pathway 7. Afterwards, the instillator 21 is pressed or rubbed so that a part of the dissolving liquid contained in the instillator 21 is transferred into the medicator 31 through the communicating pathway 7 via the germ-trapping filter 5, and the medication in the medicator 31 is dissolved in the thus-transferred dissolving liquid. Then, the medicator 31 is pressed or rubbed so that the thus-dissolved medication therein is transferred into the instillator 21 through the communicating pathway 7 via the germ-trapping filter 5. Even though the solution of the medication prepared in the medicator 31 contains germs, the inside of the instillator 21 is not contaminated by such germs since the solution is transferred into the instillator 21 via the germ-trapping filter 5. After all the solution in the medicator 31 has been transferred into the instillator 21, the communicating needle 33 is drawn from the connecting means 24 so that the medicator 31 is separated from the instillator 21. Then, as shown in FIG. 7, a dripping kit is fitted into the outlet member 22, through which the solution of the medication is administered to a patient by drip injection.

Figure 8:
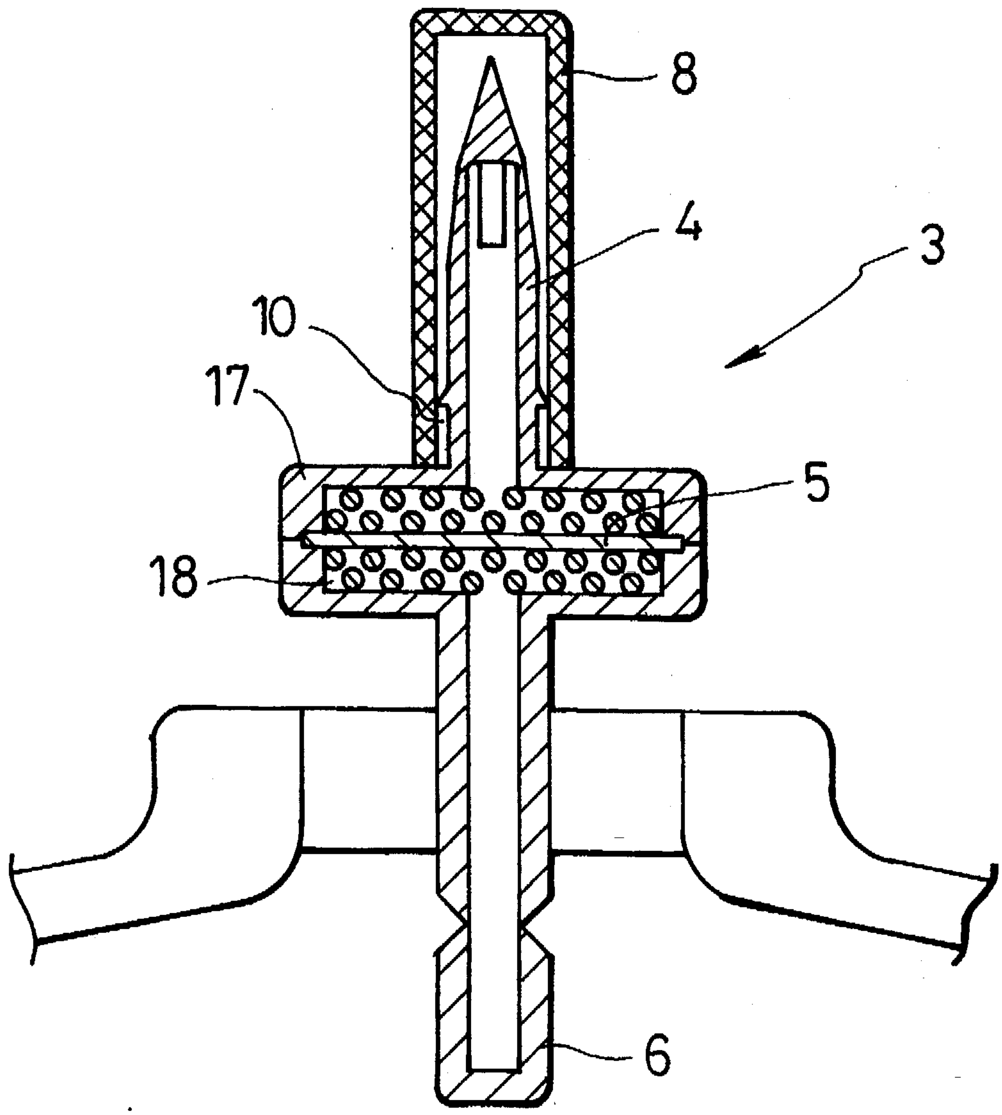
FIG. 8 is a sectional view showing one example of the medicator-connecting mouth of the instillator.

FIG. 8 shows one example of the medicator-connecting mouth 3 of the instillator of the present invention. In this figure, the germ-trapping filter 5 is fixed to a filter holder 17. It is preferred that, in the inside of the filter holder part 17, both sides of the germ-trapping filter 5 are supported by a filter support 18. When the pharmaceutical liquid passes through the germ-trapping filter 5, a filtration pressure is imparted to the germ-trapping filter 5 so that the filter 5 is deformed toward the downstream side. When the filtration pressure is large, then the germ-trapping filter 5 is deformed greatly and, as a result, partly adheres to the filter holder 17 with the result that the filtration efficiency is worsened or the filter 5 itself is broken. Therefore, if the filter support is provided at the downstream side of the germ-trapping filter, it may prevent the deformation of the filter 5 due to the filtration pressure. Thus, the filter support may solve the above-mentioned problem. The filter support 18 may have any structure that supports the germ-trapping filter 5 and ensures the pathway for the pharmaceutical liquid. For instance, employable are a network structure, a slit structure, etc.

Figure 9:
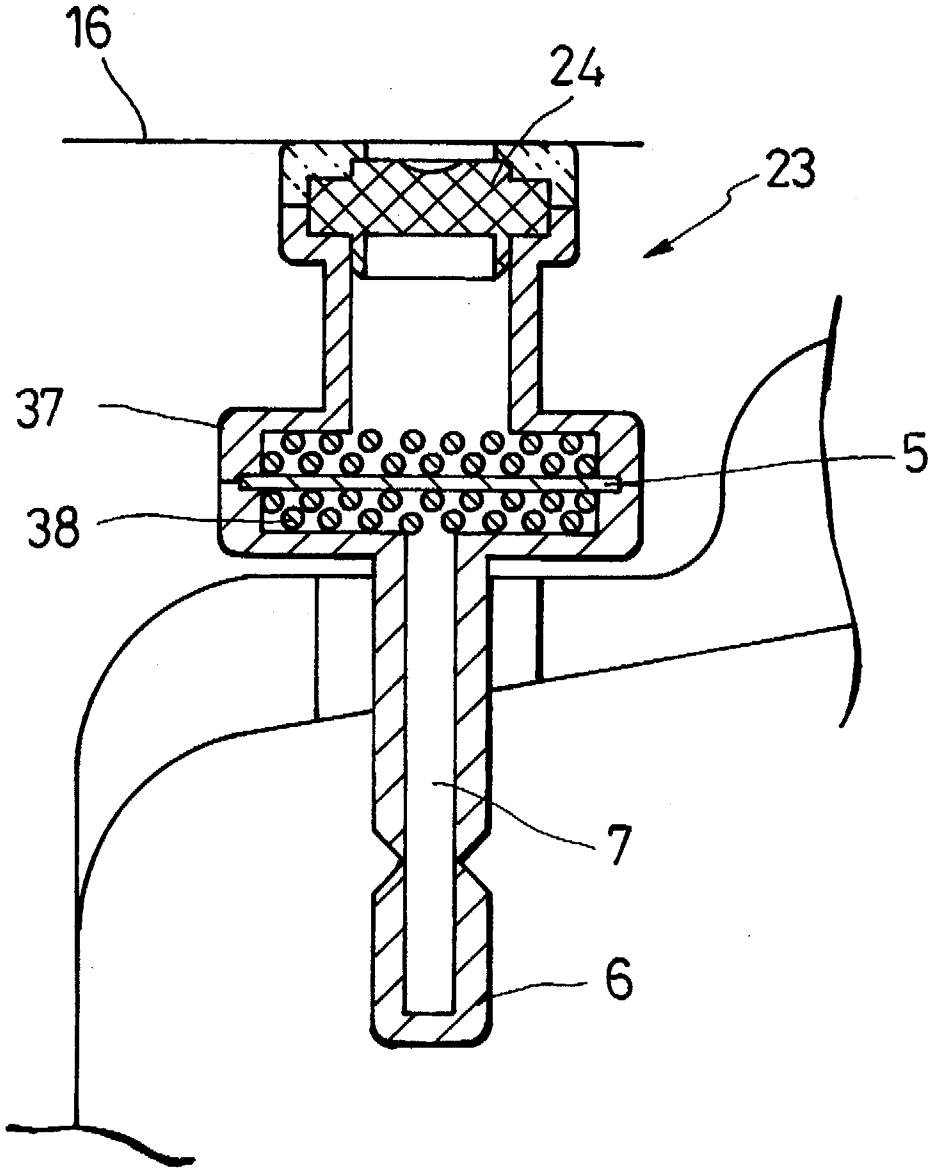
FIG. 9 is a sectional view showing another example of the medicator-connecting mouth of the instillator.

FIG. 9 shows another example of the medicator-connecting mouth 23 of the instillator of the present invention. Also in this example, it is preferred that, in the inside of the filter holder 37, both sides of the germ-trapping filter 5 are supported by the filter support 38, like in the medicator-connecting mouth 3 illustrated by FIG. 8.

Figure 10:
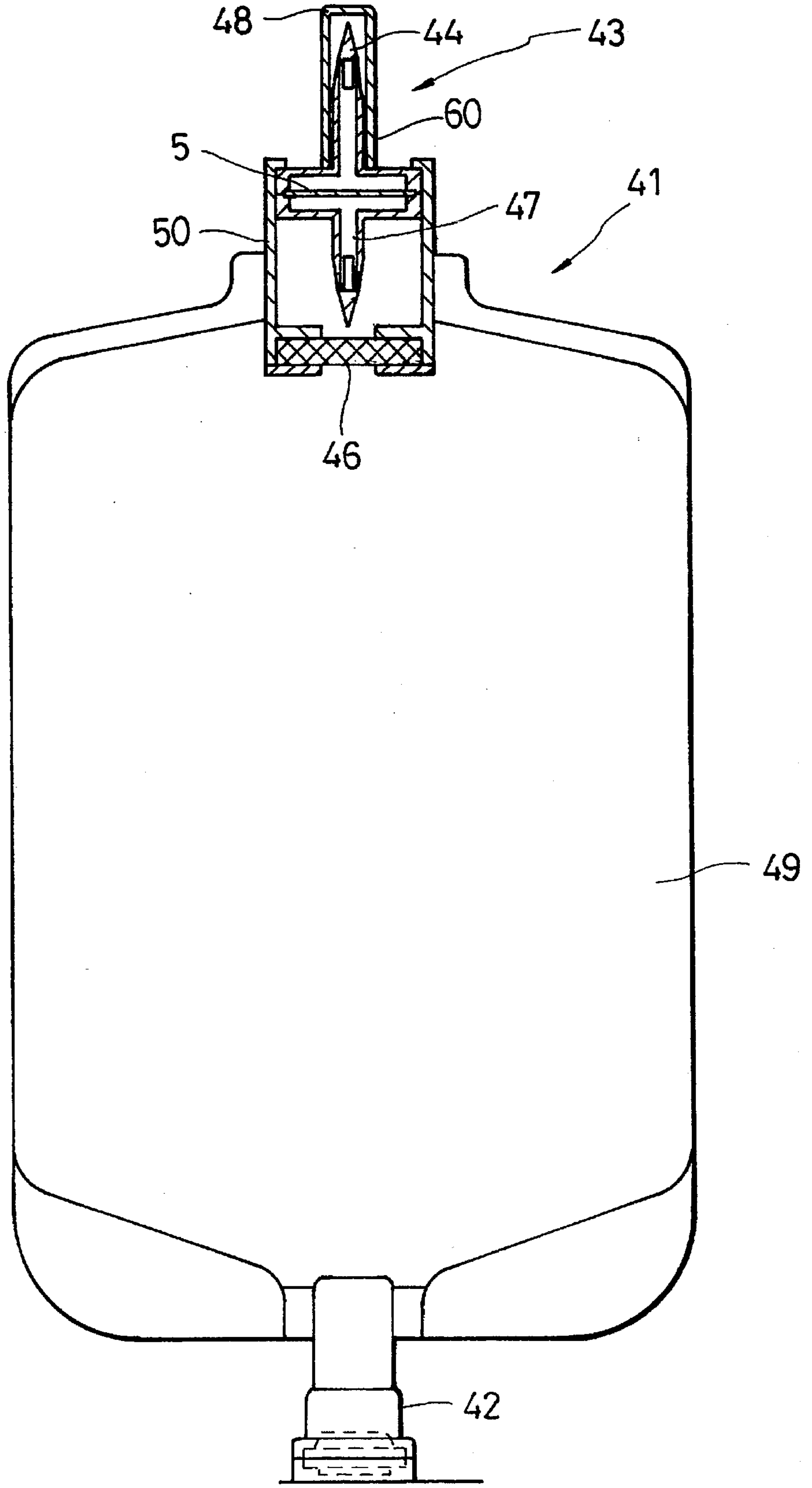
FIG. 10 is a sectional view showing an essential part of the third embodiment of the instillator.

FIG. 10 shows the third embodiment of the instillator 41 of the present invention. The instillator 41 is composed of a body 49, an outlet member 42 and a medicator-connecting mouth 43. The medicator-connecting mouth 43 is composed of a connecting means 44, a germ-trapping filter 5, a sealing means 46, a communicating pathway 47 and a port 50. The germ-trapping filter 5 is disposed in the middle of the communicating pathway 47. The connecting means 44 in this embodiment has hollow communicating needles made of a synthetic resin at the both sides of the germ-trapping filter 5. In addition, the connecting means 44 is fitted in the inside of the port 50, through which no liquid passes, and the means 44 is slidable in the port 50. One communicating needle is covered with a cap 48. The sealing means 46 is a rubber stopper, which is disposed at one end of the port 50. Also in this embodiment, the instillator 41 is made of a tube formed by inflation molding, like that in the first embodiment.

Figure 11:
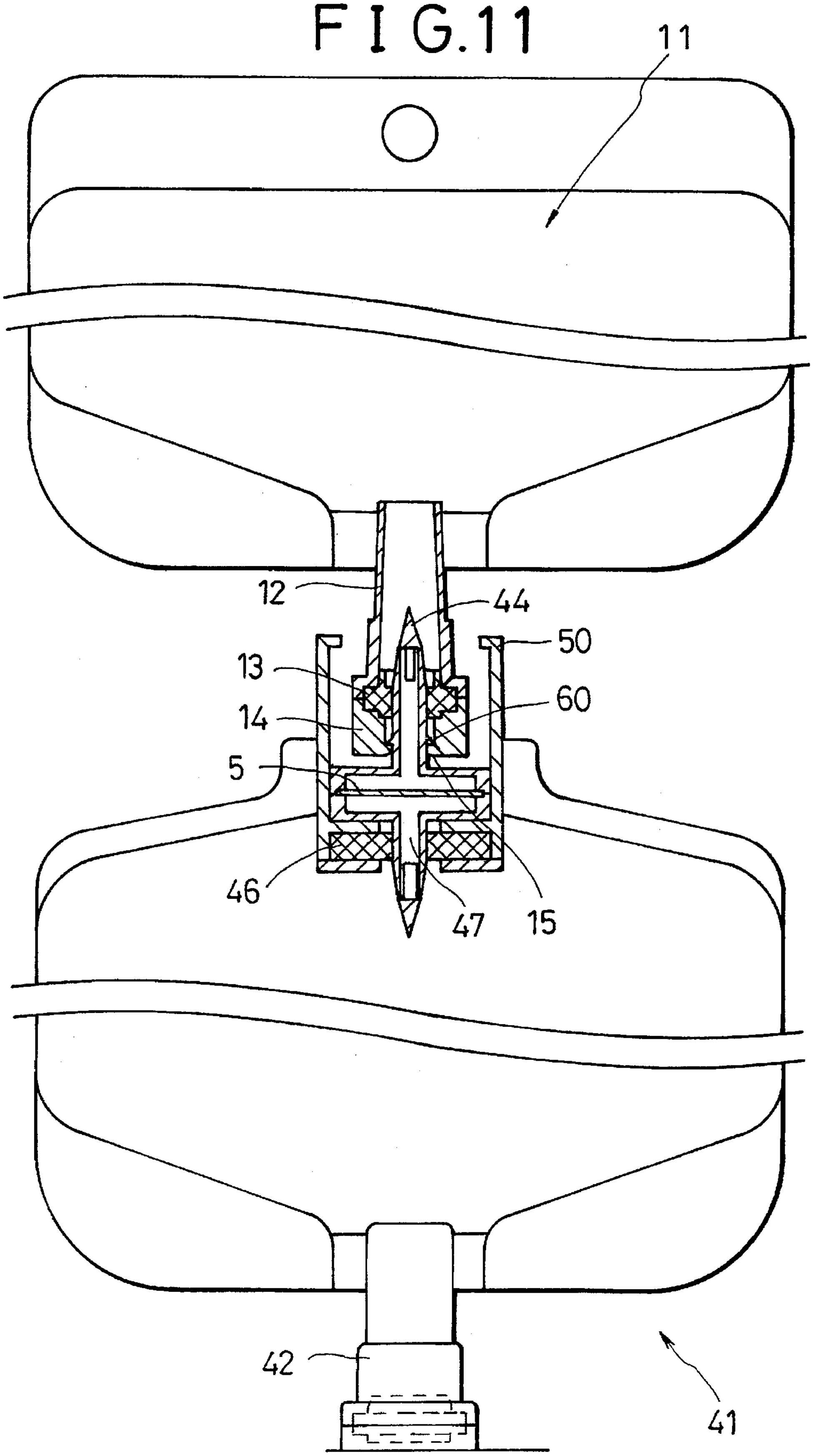
FIG. 11 is a sectional view showing an essential part of the connection between the third embodiment of the instillator to the first embodiment of the medicator.

FIG. 11 shows the connection of the sealed instillator 41 containing therein a dissolving liquid sterilized by autoclave sterilization to the sealed medicator 11 containing therein a medication. The cap 48 is removed from one communicating needle, and the other communicating needle, namely, the connecting means 44 is put into the stopper 13, and it is inserted into the mouth of the medicator until the projection 60 of the connecting means runs over the projection 15 of the stopper cap. In addition, the connecting means 44 is pushed toward the sealing means 46, by which the communicating needle is made to pierce the sealing means, namely the rubber stopper. Thus, the inside of the instillator 41 communicates with the inside of the medicator 11 via the communicating pathway 47. Afterwards, the instillator 41 is pressed or rubbed so that a part of the dissolving liquid contained in the instillator 41 is transferred into the medicator 11 through the communicating pathway 47 via the germ-trapping filter 5, and the medication in the medicator 11 is dissolved in the thus-transferred dissolving liquid. Then, the medicator 11 is pressed or rubbed so that the thus-dissolved medication therein is transferred into the instillator 41 through the communicating pathway 47 via the germ-trapping filter 5. Even though the solution of the medication prepared in the medicator 11 contains germs, the inside of the instillator 41 is not contaminated by such germs since the solution is transferred into the instillator 41 via the germ-trapping filter 5. A dripping kit is fitted into the outlet member 42 of the instillator 41, through which the solution of the medication is administered to a patient by drip injection.

Next, one test example using the instillator 1 of the first embodiment of the present invention and the medicator 11 will be mentioned below. Forty instillator samples were prepared by putting 100 ml of distilled water into the instillator 1 having, as the germ-trapping filter, membrane filter FR-20 made of regenerated cellulose (made by Fuji Photo Film Co.) followed by sealing it. These instillator samples were sterilized in an autoclave at 110° C. for 40 minutes. Next, 40 medicator samples were prepared, by putting thioglycollic acid medium (2) into the medicator 11, followed by sealing it; and 40 medicator samples were prepared, by putting glucose-peptone medium into the same, followed by sealing it. The instillator 1 containing distilled water therein was connected to the medicator 11 containing thioglycollic acid medium (2) therein, to prepare 20 combination samples. In each of these combination samples, the medium (2) was dissolved in the distilled water and the resulting solution was transferred into the instillator 1. In the same manner, 20 combination samples were prepared by connecting the instillator 1 containing distilled water therein to the medicator 11 containing glucose-peptone medium therein. After the medium was dissolved in the distilled water, the resulting solution was transferred into the instillator 1, also in each of these 20 combination samples. As a comparative test example, instillators A were prepared by removing the germ-trapping filter from each of the instillators of the first embodiment of the present invention. These were filled with distilled water and then sterilized by autoclave sterilization. The instillator A containing distilled water therein was connected to the medicator 11 containing thioglycollic acid medium (2) therein, to prepare 20 combination samples. In each of these combination samples, the medium (2) was dissolved in the distilled water and the resulting solution was transferred into the instillator A. In the same manner, 20 combination samples were prepared by connecting the instillator A containing distilled water therein to the medicator 11 containing glucose-peptone medium therein. After the medium was dissolved in the distilled water, the resulting solution was transferred into the instillator A, also in each of these 20 combination samples. The combination samples containing thioglycollic acid medium (2) therein were incubated at 32° C. for 7 hours, while those containing glucose-peptone therein were incubated at 24° C. for 7 days. As a result, no germs grew in the instillators 1 containing thioglycollic acid medium (2) or glucose-peptone medium therein. As opposed to these, germs grew in 12 of the 20 instillators A containing thioglycollic acid medium (2) therein and in 9 of the 20 instillators A containing glucose-peptone medium therein.

Using the instillator of the present invention which has been explained in the above, it is possible to dissolve or dilute, in a germ-free condition, medications that cannot be sterilized through the use of heat, such as those having poor thermal stability or those whose aqueous solutions are unstable. Therefore, it may be used to safely administer such medications to patients.

What is claimed is:

1. An instillator comprising:

a hollow body having an outlet member and a medicator-connecting mouth, said connecting mouth being composed of a communicating pathway, a sealing means, a germ-trapping filter and a connecting means, said communication pathway being closed by said sealing means for separating an interior of said body and an exterior of said body, said sealing means being a breakable seal, said connecting means being a needle portion, wherein said germ-trapping filter is provided between said needle portion and said breakable seal.

2. An instillator as claimed in claim 1, wherein said germ-trapping filter comprises:

a filter member extending substantially completely across said communicating pathway; and a filter support provided on opposing sides of said filter member.

3. An instillator as claimed in claim 1, wherein said sealing means is constructed and arranged to be manually broken off by bending, thereby communicating said interior and said exterior of said hollow body.

4. An instillator as claimed in claim 1, wherein said germ-trapping filter has pores having a diameter no greater than about 0.2 μm.

* * * * *